(12) United States Patent
Bafile et al.

(10) Patent No.: US 10,792,457 B2
(45) Date of Patent: Oct. 6, 2020

(54) COLLAPSIBLE HUMIDIFIER

(71) Applicant: KONINKLIJKE PHILIPS N.V., Eindhoven (NL)

(72) Inventors: Anthony Jon Bafile, Pittsburgh, PA (US); Richard James McKenzie, Butler, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 244 days.

(21) Appl. No.: 15/740,117

(22) PCT Filed: Jun. 16, 2016

(86) PCT No.: PCT/IB2016/053555
§ 371 (c)(1),
(2) Date: Dec. 27, 2017

(87) PCT Pub. No.: WO2017/001958
PCT Pub. Date: Jan. 5, 2017

(65) Prior Publication Data
US 2018/0193585 A1    Jul. 12, 2018

Related U.S. Application Data

(60) Provisional application No. 62/185,886, filed on Jun. 29, 2015.

(51) Int. Cl.
| | | |
|---|---|---|
| A61M 16/16 | (2006.01) | |
| A61M 16/10 | (2006.01) | |
| A61M 16/20 | (2006.01) | |
| A61M 16/00 | (2006.01) | |

(52) U.S. Cl.
CPC .......... *A61M 16/16* (2013.01); *A61M 16/024* (2017.08); *A61M 16/109* (2014.02);
(Continued)

(58) Field of Classification Search
CPC ..... A61M 16/16; A61M 16/109; B65D 37/00; B01D 47/02; B01F 3/0407; F24F 6/12;
(Continued)

(56) References Cited

U.S. PATENT DOCUMENTS

| | | |
|---|---|---|
| 5,148,802 A | 9/1992 | Sanders et al. |
| 5,313,937 A | 5/1994 | Zdrojkowski |

(Continued)

FOREIGN PATENT DOCUMENTS

| | | |
|---|---|---|
| CN | 203736193 A | 4/2014 |
| WO | 2008011660 A1 | 1/2008 |

(Continued)

*Primary Examiner* — Samchuan C Yao
*Assistant Examiner* — Margaret M Luarca

(57) ABSTRACT

A humidifier for an airway pressure support system, includes a base, a number of side walls extending from the base, and a top wall provided opposite the base, wherein the base, the number of side walls, and the top wall are made from an elastomeric material and at least partially define an internal chamber for receiving and holding a liquid. The humidifier also includes a plurality of support structures provided on or within the humidifier, each support structure extending along at least the number of side walls, wherein the humidifier is structured to collapse from an initial, expanded condition to a collapsed condition when a compressive force is applied to the top wall in the initial, expanded condition and to automatically return to the initial, expanded condition when the force is removed.

20 Claims, 6 Drawing Sheets

(52) U.S. Cl.
CPC ....... *A61M 16/1075* (2013.01); *A61M 16/204* (2014.02); *A61M 2205/0216* (2013.01); *A61M 2205/3331* (2013.01); *A61M 2205/3368* (2013.01)

(58) Field of Classification Search
CPC ...... F24F 6/14; F24F 6/025; F24F 6/00; F24F 2006/008; F24F 1/04; F25D 2323/061; Y10S 261/65
See application file for complete search history.

(56) References Cited

U.S. PATENT DOCUMENTS

| | | |
|---|---|---|
| 5,433,193 A | 7/1995 | Sanders et al. |
| 5,632,269 A | 5/1997 | Zdrojkowski |
| 5,803,065 A | 9/1998 | Zdrojkowski et al. |
| 6,029,664 A | 2/2000 | Zdrojkowski et al. |
| 6,539,940 B2 | 4/2003 | Zdrojkowski et al. |
| 6,626,175 B2 | 9/2003 | Jafari et al. |
| 7,011,091 B2 | 3/2006 | Hill et al. |
| 2005/0022810 A1 | 2/2005 | Fosella |
| 2007/0045152 A1 | 3/2007 | Kwok et al. |
| 2007/0182034 A1 | 8/2007 | Okada et al. |
| 2008/0173305 A1 | 7/2008 | Frater |
| 2010/0236552 A1 | 9/2010 | Kwok et al. |
| 2016/0206512 A1* | 7/2016 | Chhikara .......... A61M 5/31513 |

FOREIGN PATENT DOCUMENTS

| | | |
|---|---|---|
| WO | 2013061187 A1 | 5/2013 |
| WO | 2014207730 A2 | 12/2014 |

* cited by examiner

COLLAPSIBLE HUMIDIFIER

CROSS-REFERENCE TO PRIOR APPLICATIONS

This application is the U.S. National Phase application under 35 U.S.C. § 371 of International Application Serial No. PCT/IB2016/053555, filed on 16 Jun. 2016, which claims the benefit of U.S. Application Ser. No. 62/185,886, filed on 29 Jun. 2015. These applications are hereby incorporated by reference herein.

BACKGROUND OF THE INVENTION

1. Field of the Invention

The present invention relates to airway pressure support systems, and, more particularly, to a portable, collapsible humidifier for use with an airway pressure support systems.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

It is well known to treat sleep disordered breathing by applying a positive air pressure (PAP) to the patient's airway. This positive pressure effectively "splints" the airway, thereby maintaining an open passage to the lungs. In one type of PAP therapy, known as continuous positive air pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Humidifiers are frequently provided between or integral with a PAP machine and the user interface in order to humidify the otherwise relatively-dry compressed air generated by the PAP machine. Typically, humidifiers can be categorized as passover types or non-passover types. In a passover type of humidifier, water is contained in a reservoir that may or may not be heated. While the water is allowed to evaporate to produce vapor within the reservoir, breathing gas is passed over the surface of the water in order to add moisture to the breathing gas before it is delivered to the patient.

When patients that use PAP therapy travel, they are often faced with the inconvenience of travelling with their bulky PAP equipment. To save space and/or weight, some patients will leave their humidifier behind. However, for many patients, the humidifier is required for a comfortable night of sleep.

SUMMARY OF THE INVENTION

In one embodiment, a humidifier for an airway pressure support system is provided. The humidifier includes a base, a number of side walls extending from the base, and a top wall provided opposite the base, wherein the base, the number of side walls, and the top wall are made from an elastomeric material and at least partially define an internal chamber for receiving and holding a liquid. The humidifier also includes a plurality of support structures provided on or within the humidifier, each support structure extending along at least the number of side walls, wherein the humidifier is structured to collapse from an initial, expanded condition to a collapsed condition when a compressive force is applied to the top wall in the initial, expanded condition and to automatically return to the initial, expanded condition when the force is removed.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
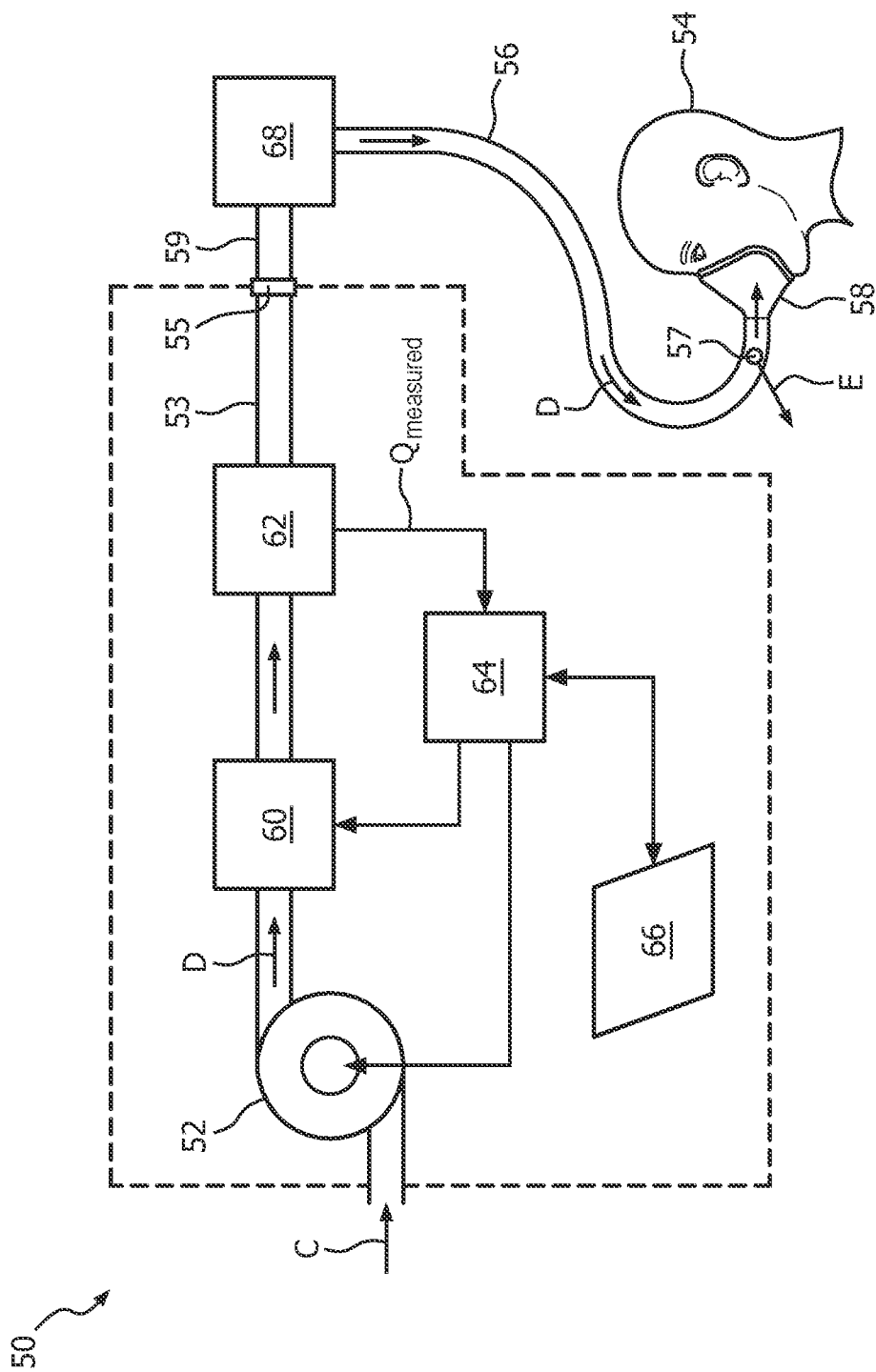
FIG. 1 is a schematic diagram of a pressure support system according to one particular, non-limiting embodiment in which the present invention in its various embodiments may be implemented.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "elastomeric material" shall mean a material that exhibits elastic but not viscous characteristics when undergoing deformation, and, as a result, does not exhibit time dependent strain. Thus, the term "elastomeric material" as used herein refers to a material that deforms under the influence of an applied stress and returns instantaneously to its original state once the stress is removed, thereby recovering from substantially all of the deformation.

As used herein, the terms "instantaneous" and "instantaneously" shall mean occurring with almost no delay; completed within a moment or an instant; immediate.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of a pressure support system 50 according to one particular, non-limiting exemplary embodiment in which the present invention in its various embodiments may be implemented. Referring to FIG. 1, pressure support system 50 includes a gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of a patient 54 at relatively higher and lower pressures, i.e., generally equal to or above ambient atmospheric pressure. In the exemplary embodiment, gas flow generator 52 is capable of providing a flow of breathing gas ranging in pressure from 3-30 cmH2O. The pressurized flow of breathing gas, generally indicated by arrow D from gas flow generator 52, is delivered via a delivery tube 56 to a breathing mask or patient interface 58 of any known construction, which is typically worn by or otherwise attached to patient 54 to communicate the flow of breathing gas to the airway of patient 54. Delivery tube 56 and patient interface device 58 are typically collectively referred to as a patient circuit.

Pressure support system 50 shown in FIG. 1 is what is known as a single-limb system, meaning that the patient circuit includes only delivery tube 56 connecting patient 54 to pressure support system 50. As such, an exhaust vent 57 is provided in delivery tube 56 for venting exhaled gases from the system as indicated by arrow E. It should be noted that exhaust vent 57 can be provided at other locations in addition to or instead of in delivery tube 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery tube and an exhaust tube connected to patient 54. In a two-limb system (also referred to as a dual-limb system), the exhaust tube carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal/oral mask. It is to be understood, however, that patient interface 58 can include a nasal mask, nasal pillows, a tracheal tube, an endotracheal tube, or any other device that provides a suitable gas flow communicating function. Also, for purposes of the present invention, the phrase "patient interface" can include delivery tube 56 and any other structures that couple the source of pressurized breathing gas to patient 54.

In the illustrated embodiment, pressure support system 50 includes a pressure controller in the form of a valve 60 provided in internal delivery tube 53 provided in the main housing of pressure support system 50. Valve 60 controls the pressure of the flow of breathing gas from gas flow generator 52 that is delivered to patient 54. For present purposes, gas flow generator 52 and valve 60 are collectively referred to as a pressure generating system because they act in concert to control the pressure and/or flow of gas delivered to patient 54. However, it should be apparent that other techniques for controlling the pressure of the gas delivered to patient 54, such as varying the blower speed of gas flow generator 52, either alone or in combination with a pressure control valve, are contemplated by the present invention. Thus, valve 60 is optional depending on the technique used to control the pressure of the flow of breathing gas delivered to patient 54.

If valve 60 is eliminated, the pressure generating system corresponds to gas flow generator 52 alone, and the pressure of gas in the patient circuit is controlled, for example, by controlling the motor speed of gas flow generator 52.

Pressure support system 50 further includes a flow sensor 62 that measures the flow of the breathing gas within delivery tube 53 and delivery tube 56. In the particular embodiment shown in FIG. 1, flow sensor 62 is interposed in line with delivery tubes 53 and 56, most preferably downstream of valve 60. Flow sensor 62 generates a flow signal, Qmeasured, that is provided to a controller 64 and is used by controller 64 to determine the flow of gas at patient 54 (Qpatient).

Techniques for calculating Qpatient based on Qmeasured are well known, and take into consideration the pressure drop of the patient circuit, known leaks from the system, i.e., the intentional exhausting of gas from the circuit as indicated by arrow E in FIG. 1, and unknown leaks from the system, such as leaks at the mask/patient interface. The present invention contemplates using any known or hereafter developed technique for calculating leak flow Qleak, and using this determination in calculating Qpatient based on Qmeasured. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 54 are contemplated by the present invention, such as, without limitation, measuring the flow directly at patient 54 or at other locations along delivery tube 56, measuring patient flow based on the operation of gas flow generator 52, and measuring patient flow using a flow sensor upstream of valve 60.

Controller 64 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 50, including automatically controlling humidity as described in greater detail herein.

An input/output device 66 is provided for setting various parameters used by pressure support system 50, as well as for displaying and outputting information and data to a user, such as a clinician or caregiver.

In the illustrated, non-limiting exemplary embodiment of the present invention, pressure support system 50 essentially functions as a CPAP pressure support system, and, therefore, includes all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Finally, in the illustrated embodiment, pressure support system 50 includes a humidifier 68 that is separate from the main housing of pressure support system 50 and that may be selectively coupled to the main housing of pressure support system 50 as desired. In particular, humidifier 68 may be coupled to the main housing of pressure support system 50 within the gas delivery path at a location between an output port 55 of the main housing of pressure support system 50 via intermediate tubing 59 and delivery tube 56. Humidifier 68 is coupled to and controlled by controller 64, and thus further improves patient comfort by providing moisture in the supplied breathing gas. In the exemplary embodiment, described in detail herein, humidifier 68 is a passover type humidifier.

Figure 2:
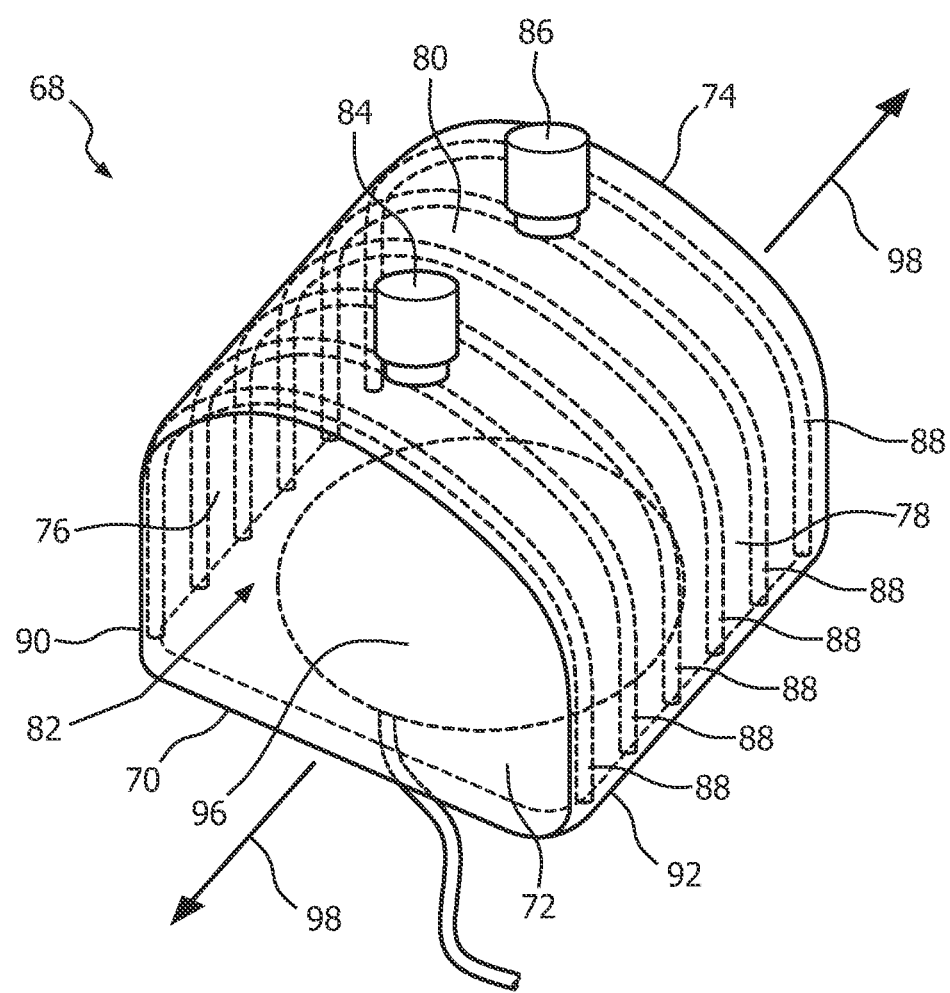
FIG. 2 is an isometric view.
Figure 3:
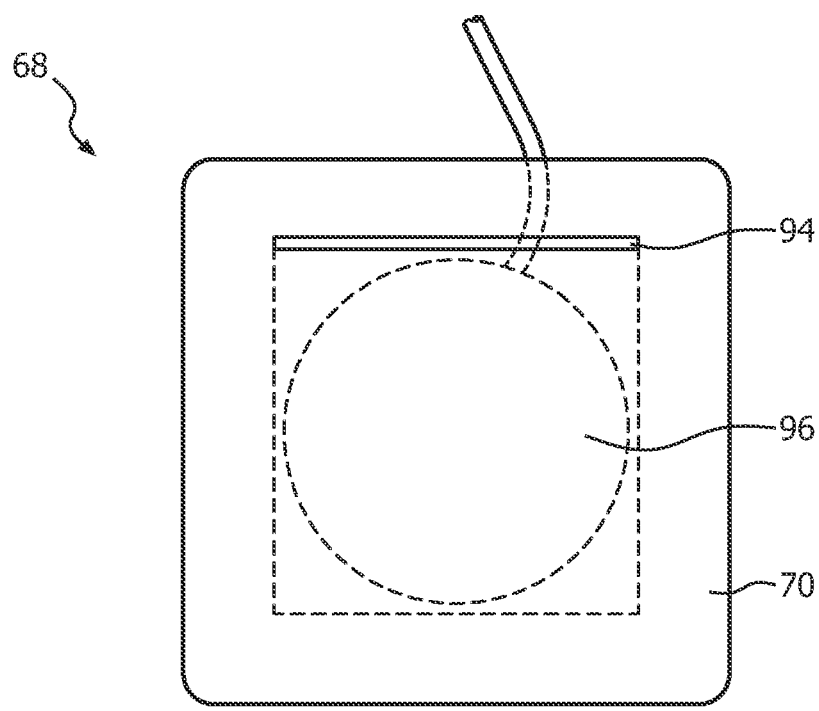
FIG. 3 is a bottom plan view and FIG. 4 is a cross-sectional view of a humidifier according to an exemplary embodiment that may be used in the pressure support system of FIG. 1.
Figure 4:
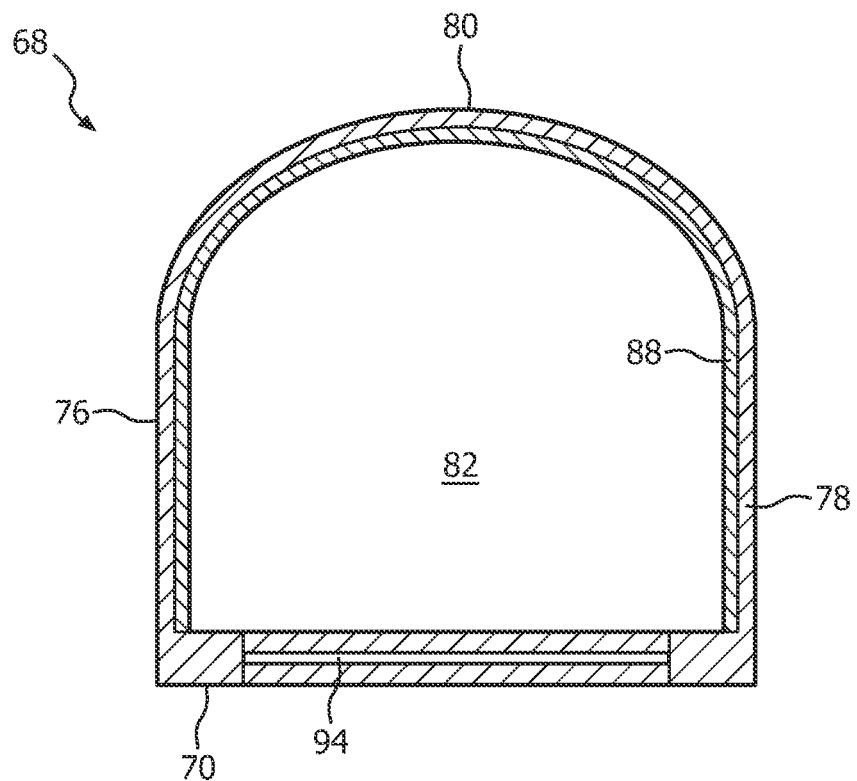

FIG. 2 is an isometric view, FIG. 3 is a bottom plan view and FIG. 4 is a cross-sectional view of humidifier 68 according to an exemplary embodiment of the present invention that may be used to implement humidifier 68 of pressure support system 50. As described herein, humidifier 68 is made of an elastomeric material and is structured such that, in order to save space and make it convenient for travel, it may be easily collapsed and rolled by a user as needed to reduce the space it occupies. Humidifier 68 is also structured such that, when the forces applied to make it collapse and/or rolled are removed, it will instantaneously return to its original shape without having to be manually expanded by the user.

Referring to FIGS. 2, 3 and 4, humidifier 68 includes a base 70, a front wall 72, a rear wall 74, a first side wall 76, a second side wall 78 opposite the first side wall 76, and a top wall 80 opposite base 70. Humidifier 68 thus forms an internal chamber 82 that, as described herein, is structured to receive and hold water therein for purposes of humidifying breathing gas delivered to patient 54. Base 70, front wall 72, rear wall 74, first side wall 76, second side wall 78, and top wall 80 are all made from an elastomeric material, such as, without limitation, silicone. In the exemplary embodiment, base 70, front wall 72, rear wall 74, first side wall 76, second side wall 78, and top wall 80 are made from a material having a durometer of 20-80 Shore A, or in one particular embodiment 40-50 Shore A.

As seen in FIG. 2, an inlet port/coupling 84 and an outlet port/coupling 86 are coupled to top wall 80 in order to provide fluid access to internal chamber 82. Inlet port/coupling 84 is structured to be fluidly coupled to intermediate tubing 59 in order to fluidly couple humidifier 68 to delivery tube 53 within the main housing of pressure support system 50, and outlet port/coupling 86 is structured to be fluidly coupled to delivery tube 56 in order to fluidly couple humidifier 68 to patient interface 58. As a result, breathing gas generated by gas flow generator 52 is able to be passed through humidifier 68 and over the water contained therein for humidification and then on to patient 54 through delivery tube 56 and patient interface 58.

Furthermore, humidifier 68 includes a number of support structures which facilitate the ability of humidifier 68 to automatically return to its relaxed, non-collapsed state when collapsing forces are removed therefrom. In particular, in the exemplary embodiment shown in FIGS. 2, 3 and 4, humidifier 68 includes a plurality of rib members 88 which are provided on or within humidifier 68 and which, in the non-limiting illustrated exemplary embodiment, each extend in an arced fashion from a first side 90 of base 70 to a second side 92 of base 70 along first side wall 76, top wall 80 and second side wall 78. In the exemplary embodiment, rib members 88 are provided on the internal surface of first side wall 76, top wall 80 and second side wall 78 A humidifier (68, 68', 100, 100') for an airway pressure support system (50), includes a base (70, 102), a number of side walls (76, 78, 104) extending from the base, and a top wall (80, 106) provided opposite the base, wherein the base, the number of side walls, and the top wall are made from an elastomeric material and at least partially define an internal chamber (82) for receiving and holding a liquid. The humidifier also includes a plurality of support structures (88, 88', 112, 114, 118, 120) provided on or within the humidifier, each support structure extending along at least the number of side walls, wherein the humidifier is structured to collapse from an initial, expanded condition to a collapsed condition when a compressive force is applied to the top wall in the initial, expanded condition and to automatically return to the initial, expanded condition when the force is removed, although it will be appreciated that other configurations are also possible. For example, rib members 88 may also be provided partially or completely within first side wall 76, top wall 88 and second side wall 78, or on an external surface of first side wall 76, top wall 80 and second side wall 78.

In the exemplary embodiment of FIG. 2, rib members 88 are parallel to one another (lying in parallel planes), are perpendicular to the longitudinal axis 98 of humidifier 68, and are spaced along the longitudinal axis 98. As described herein, this implementation is just one example of how rib members 88 may be configured, and alternative configurations are possible within the scope of the present invention. For example, and without limitation, rib members 88 may be woven, braided or provided in a cross hatched/lattice like structure. These alternate implementations would thus allow for different roll up configurations.

In addition, rib members 88 may have any of a number of different structures. For example, rib members 88 may be co-molded with the remainder of humidifier 68 in the form of thickened sections of elastomeric material used to form base 70, front wall 72, rear wall 74, first side wall 76, second side wall 78, and top wall 80. Alternatively, rib members 88 may be formed from spring steel and or a flexible plastic spring material onto which the remainder of humidifier 68 is over molded.

Moreover, as seen in FIGS. 3 and 4, base 70 is thicker than front wall 72, rear wall 74, first side wall 76, second side wall 78, and top wall 80 and is provided with a pocket 94 that is accessible from the bottom of humidifier 68. Pocket 94 is structured and configured to receive and hold an electric/electronically controlled heating plate 96 that is structured to be operatively connected to controller 64 to control the operation thereof. As will be appreciated, when internal chamber 82 is filled with water, heating plate 96 may be used to generate heat which will be conducted through base 70 to heat the water to a desired temperature. Pocket 94 is advantageous in that it enables heating plate 96 to be inserted into and removed from humidifier 68 as desired, which will, as described below, facilitate the collapsing and rolling of humidifier 68 for travel purposes.

Figure 5:
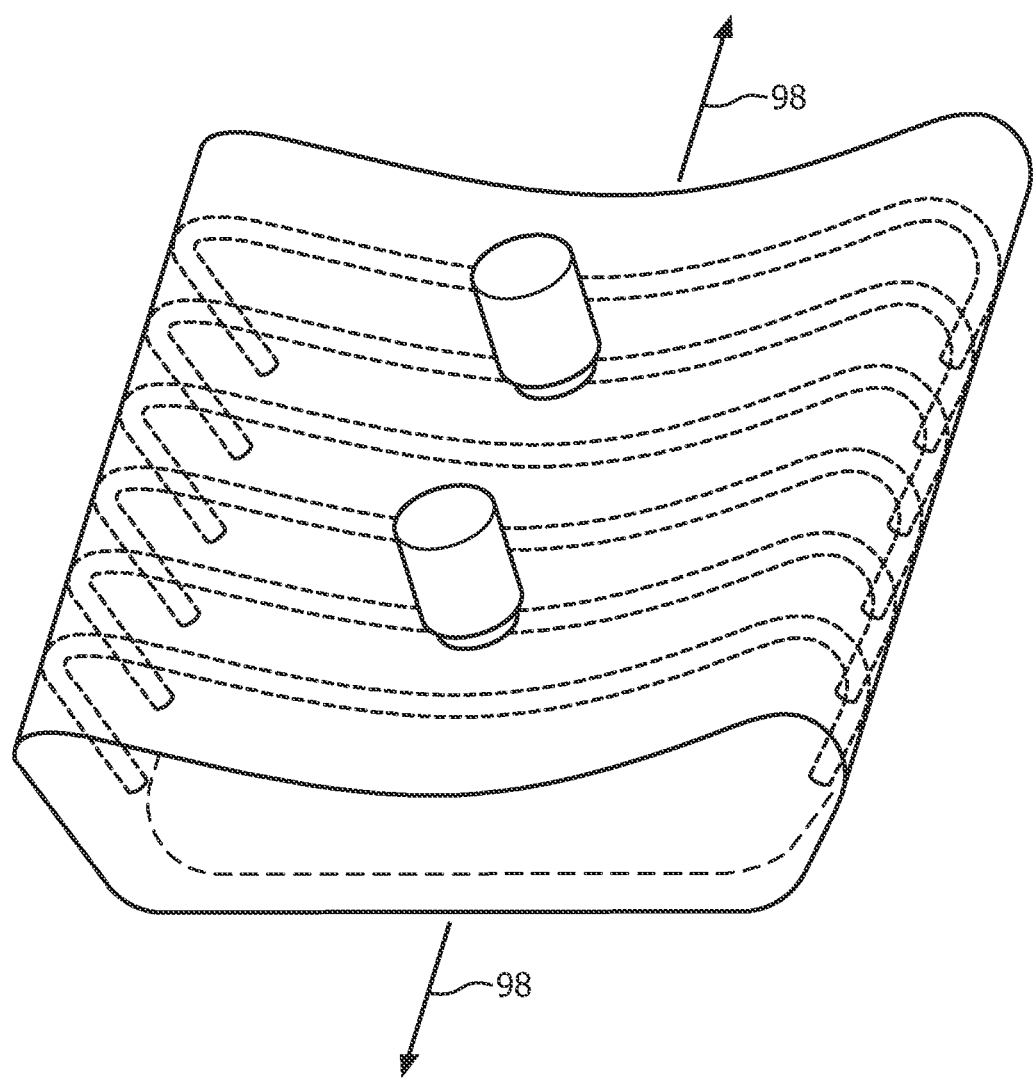
FIG. 5 is an isometric view of the humidifier of FIGS. 2, 3 and 4 in a collapsed condition.

In operation, when a user desires to travel with humidifier 68, the user will preferably remove heating plate 96 from pocket 94. The user will then apply a force to top wall 80 in order to collapse humidifier 68 as shown in FIG. 5. The user may then roll humidifier 68 up along the longitudinal axis 98 thereof in order to further decrease the space occupied by humidifier 68. Since, as described elsewhere herein, humidifier 68 is structured to automatically return to its non-collapsed state when collapsing forces are removed, it will be necessary to employ a mechanism, such as a band, a tie, or some kind of weight (e.g. the main housing of pressure support system 50 or another object that the user is packing for travel), to maintain the humidifier 68 in its collapsed state for travel.

When the user has reached his or her destination and wished to use humidifier 68, the band, tie or weight may be removed, thereby allowing humidifier 68 to return to its expanded, non-collapsed state as shown in FIG. 2. The user may then insert heating plate 96 into pocket 94 and couple heating plate 96 to controller 64. The user may then fill internal chamber 82 with a volume of water through one of the ports/couplings 84, 86. The user may then attach inlet port/coupling 84 to outlet port 55 of the main housing of pressure support system 50 using intermediate tubing 59, and attach outlet port/coupling 86 to delivery tube 56. Humidifier 68 will then be in a condition wherein it is operatively coupled to the main housing of pressure support system 50 so that it can be used to humidify the breathing gas that is generated by gas flow generator 52 and delivered to patient 54 through delivery tube 56 and patient interface 58.

Figure 6:
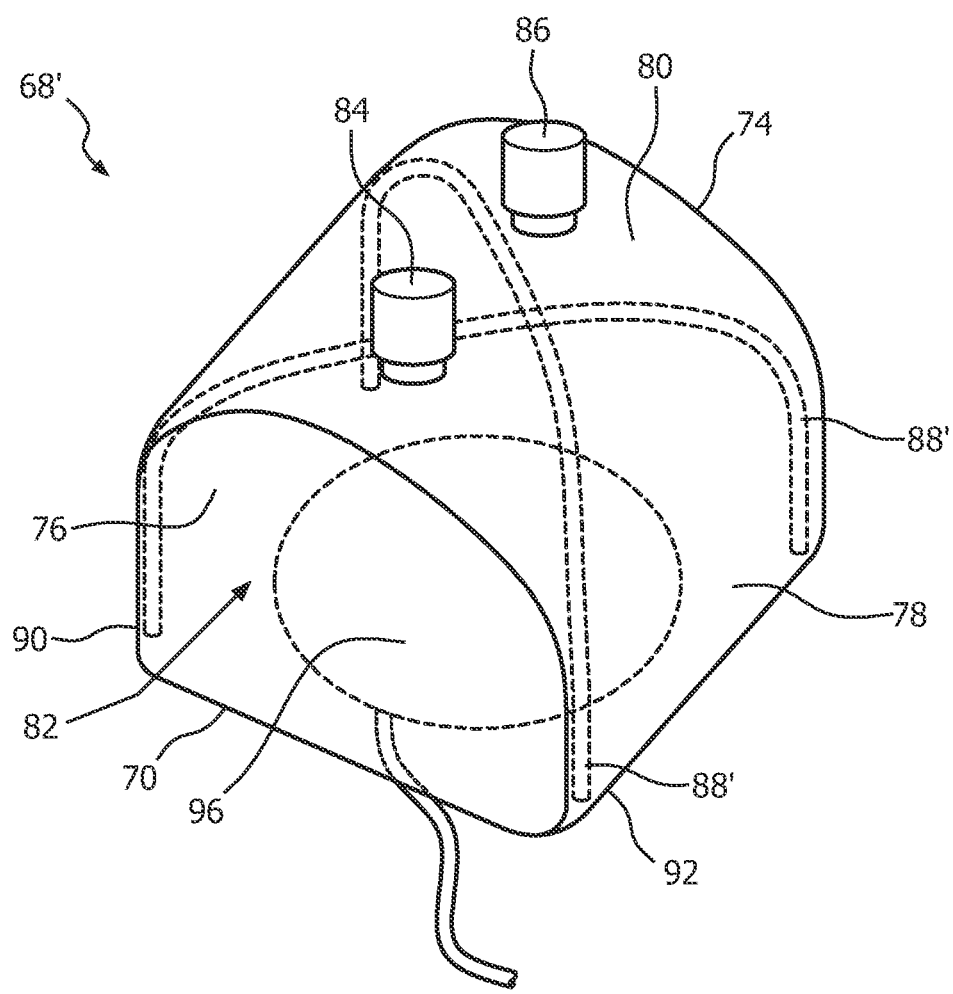
FIG. 6 is an isometric view of a humidifier according to an alternative exemplary embodiment that may be used in the pressure support system of FIG. 1.

FIG. 6 is an isometric view of a humidifier 68' according to an alternative exemplary embodiment that may be used in place of humidifier 68. Humidifier 68' includes a number of the same components as humidifier 68, and like components are labeled with like reference numerals. Humidifier 68' includes alternative rib members 88' to facilitate the ability of humidifier 68' to automatically return to an expanded, non-collapsed state when collapsing forces as described elsewhere herein are removed therefrom. In particular, humidifier 68' includes a first rib member 88' that extends diagonally from first side 90 of base 70 to second side 92 of base 70 along first side wall 76, top wall 80 and second side wall 78, and a second rib member 88' that extends diagonally from second side 92 of base 70 to first side 90 of base 70 along second side wall 78, top wall 80 and first side wall 76 in a manner wherein, as seen in FIG. 6, the first rib member 88' and the second rib member 88' crisscross at a central portion of top wall 80.

Figure 7:
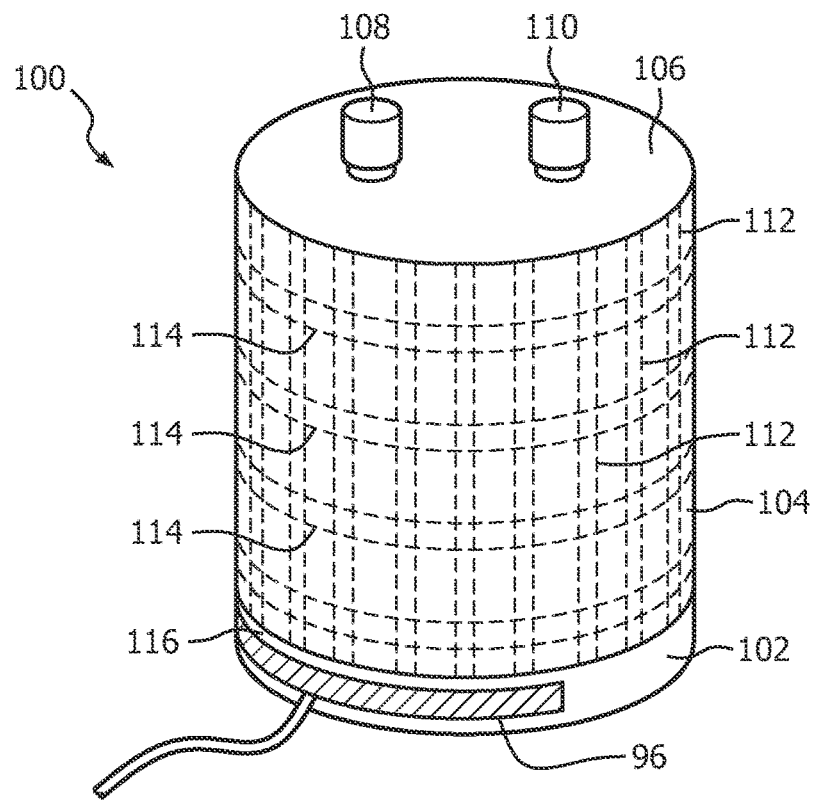
FIG. 7 is an isometric view of a humidifier according to another alternative exemplary embodiment that may be used in the pressure support system of FIG. 1.

FIG. 7 is an isometric view of a humidifier 100 according to another alternative exemplary embodiment that may be used in place of humidifier 68. Like humidifier 68, humidifier 100 is made of an elastomeric material and is structured such that, in order to save space and make it convenient for travel, it may be easily collapsed and rolled by a user as needed to reduce the space it occupies. Humidifier 100 is also structured such that, when the forces applied to make it collapse and/or rolled are removed, it will instantaneously return to its original shape without having to be manually expanded by the user.

Humidifier 100 includes a base 102, a cylindrical side wall 104, and a top wall 106 opposite base 102. Humidifier 100 thus forms an internal chamber that is structured to receive and hold water therein for purposes of humidifying breathing gas delivered to patient 54. Base 102, side wall 104, and top wall 106 are all made from an elastomeric material, such as, without limitation, silicone. In the exemplary embodiment, that material has a durometer of 20-80 Shore A, or in one particular embodiment 40-50 Shore A. An inlet port/coupling 108 and an outlet port/coupling 110 are coupled to top wall 106 in order to provide fluid access to the internal chamber. Inlet port/coupling 108 is structured to be fluidly coupled to intermediate tubing 59 in order to fluidly couple humidifier 100 to delivery tube 53 within the main housing of pressure support system 50, and outlet port/coupling 110 is structured to be fluidly coupled to delivery tube 56 in order to fluidly couple humidifier 100 to patient interface 58. As a result, breathing gas generated by gas flow generator 52 is able to be passed through humidifier 100 and over the water contained therein for humidification and then on to patient 54 through delivery tube 56 and patient interface 58.

Like humidifier 68, humidifier 100 includes a number of support structures which facilitate the ability of humidifier 100 to automatically return to its relaxed, non-collapsed state when collapsing forces are removed therefrom. In the exemplary embodiment, humidifier 100 includes a plurality of first rib members 112 which are provided on or within side wall 104 and which each extend in a direction which is parallel to the longitudinal axis of humidifier 100, and a plurality of second rib members 114 which are provided on or within side wall 104 in which each extend in a direction which is perpendicular to the longitudinal axis of humidifier 100. In the exemplary embodiment, rib members 112 and 114 are provided on the internal surface of side wall 104, although it will be appreciated that other configurations similar to those described elsewhere herein are also possible. In addition, rib members 112, 114 may have any of a number of different structures. For example, rib members 112, 114 may be co-molded with the remainder of humidifier 100 in the form of thickened sections of elastomeric material. Alternatively, rib members 112, 114 may be formed from spring steel and or a flexible plastic spring material onto which the remainder of humidifier 100 is over molded.

Moreover, base 102 is thicker than side wall 104, and is provided with a pocket 116 that is accessible from the front of humidifier 100. Pocket 116 is structured and configured to receive and hold an electric/electronically controlled heating plate 96 as described elsewhere herein.

Figure 8:
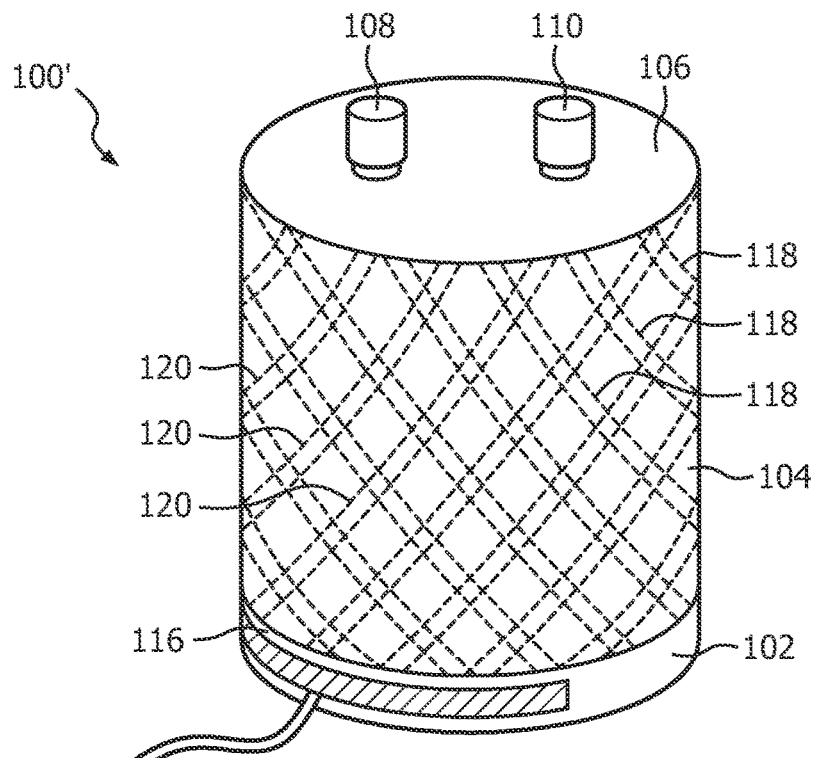
FIG. 8 is an isometric view of a humidifier according to still another alternative exemplary embodiment that may be used in the pressure support system of FIG. 1.

FIG. 8 is an isometric view of a humidifier 100' according to a further alternative exemplary embodiment that may be used in place of humidifier 68. Humidifier 100' is similar to humidifier 100, and like parts are labeled with like reference numerals. However, as seen in FIG. 8, humidifier 100' includes a plurality of first rib members 118 that extend in a first direction that is transverse to the longitudinal axis of humidifier 100' and a plurality of second rib members 120 that extend in a second direction that is transverse to the longitudinal axis of humidifier 100' such that with 118 and 120 form a crosshatching pattern.

Furthermore, it will be understood that the support structure embodiments shown in FIGS. 1,6, 7 and 8 comprising rib members 88, rib members 88', rib members 112, 114, and rib members 118, 120 are meant to be exemplary only, and that other configurations and/or structures are also possible within the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A humidifier for an airway pressure support system, comprising:
    a base;
    a number of side walls extending from the base;
    a top wall provided opposite the base, wherein the base, the number of side walls, and the top wall are made from an elastomeric material and at least partially define an internal chamber for receiving and holding a liquid; and
    a plurality of support structures provided on or within the humidifier, each support structure extending along at least the number of side walls, wherein the humidifier is structured to collapse from an initial, expanded condition to a collapsed condition when a compressive force is applied to the top wall in the initial, expanded condition and to automatically return to the initial, expanded condition when the force is removed,
    wherein the number of side walls include a first side wall extending from a first side of the base, a second side wall extending from a second side of the base, wherein the top wall is provided between the first side wall and the second side wall, and wherein each support structure extends from the first side of the base to the second side of the base along the first side wall, the top wall and the second side wall.

2. The humidifier according to claim 1, wherein the plurality of support structures comprise a plurality of rib members.

3. The humidifier according to claim 2, wherein the rib members lie in planes that are parallel to one another, wherein the rib members are perpendicular to a longitudinal axis of the humidifier, and wherein the rib members are spaced along the longitudinal axis.

4. The humidifier according to claim 2, wherein the rib members include a first rib member and a second rib member, wherein the first rib member and the second rib member crisscross at a central portion of the top wall.

5. The humidifier according to claim 2, wherein the rib members are made from the elastomeric material and comprise thickened portions of the first side wall, the top wall and the second side wall.

6. The humidifier according to claim 2, wherein the rib members each comprise a separate component attached to the first side wall, the top wall and the second side wall.

7. The humidifier according to claim 2, wherein each rib member is a metal spring member or a plastic spring member.

8. The humidifier according to claim 1, further comprising an inlet coupling and an outlet coupling, the inlet coupling and the outlet coupling providing fluid access to the internal chamber.

9. The humidifier according to claim 8, wherein the inlet coupling and the outlet coupling are provided on the top wall.

10. The humidifier according to claim 1, wherein the elastomeric material is silicone.

11. The humidifier according to claim 1, wherein the elastomeric material has a durometer of 20-80 Shore A.

12. The humidifier according to claim 1,
    wherein the plurality of support structures comprise a plurality of rib members, wherein the plurality of rib members include a first rib member and a second rib member, and wherein the first rib member and the second rib member form a crisscross pattern.

13. A pressure support system for delivering a breathing gas to a patient, wherein the pressure support system employs a humidifier according to claim 1.

14. A humidifier for an airway pressure support system, comprising:
- a base;
- a number of side walls extending from the base;
- a top wall provided opposite the base, wherein the base, the number of side walls, and the top wall are made form an elastomeric material and at least partially define an internal chamber for receiving and holding a liquid; and
- a plurality of support structures provided on or within the humidifier, each support structure extending along at least the number of side walls, wherein the humidifier is structured to collapse from an initial, expanded condition to a collapsed condition when a compressive force is applied to the top wall in the initial, expanded condition and to automatically return to the initial, expanded condition when the force is removed,
- wherein the base includes a pocket structured to removeably receive a heating plate.

15. The humidifier according to claim 14, wherein the pocket is provided in and accessible from a bottom surface of the humidifier.

16. A pressure support system for delivering a breathing gas to a patient, wherein the pressure support system employs a humidifier according to claim 14.

17. A humidifier for an airway pressure support system, comprising:
- a base;
- a number of side walls extending from the base;
- a top wall provided opposite the base, wherein the base, the number of side walls, and the top wall are made form an elastomeric material and at least partially define an internal chamber for receiving and holding a liquid; and
- a plurality of support structures provided on or within the humidifier, each support structure extending along at least the number of side walls, wherein the humidifier is structured to collapse from an initial, expanded condition to a collapsed condition when a compressive force is applied to the top wall in the initial, expanded condition and to automatically return to the initial, expanded condition when the force is removed,
- wherein the plurality of support structures comprise a plurality of rib members, and wherein the plurality of rib members include a plurality of first rib members and a plurality of second rib members wherein the first rib members and the second rib members form a crisscross pattern.

18. The humidifier according to claim 17, wherein the number of side walls include a cylindrical side wall provided between the base and the top wall.

19. A humidifier for an airway pressure support system, comprising:
- a base;
- a number of side walls extending from the base;
- a top wall provided opposite the base, wherein the base, the number of side walls, and the top wall are made form an elastomeric material and at least partially define an internal chamber for receiving and holding a liquid; and
- a plurality of support structures provided on or within the humidifier, each support structure extending along at least the number of side walls, wherein the humidifier is structured to collapse from an initial, expanded condition to a collapsed condition when a compressive force is applied to the top wall in the initial, expanded condition and to automatically return to the initial, expanded condition when the force is removed,
- wherein the plurality of support structures comprise a first and second rib members that are spaced apart along a perimeter of the base and extend upwardly away from the base, and
- wherein the collapse and the automatic return are correspondingly in opposite directions perpendicular to the perimeter of the base.

20. The humidifier according to claim 19, wherein at least two of the plurality of support structures form a crisscross pattern.

\* \* \* \* \*